(12) United States Patent
Notte et al.

(10) Patent No.: US 7,662,991 B2
(45) Date of Patent: Feb. 16, 2010

(54) PROCESS FOR THE MANUFACTURE OF AMINOALKYLENEPHOSPHONIC ACID COMPOUNDS IN THE PRESENCE OF A HETEROGENEOUS CATALYST

(75) Inventors: Patrick P. Notte, Wavre (BE); Isabelle Emmanuel Vanesse, Chastre-Villeroux (BE); Jan H. J. Van Bree, Ottenburg (BE)

(73) Assignee: Thermphos Trading GmbH, Zug (CH)

( * ) Notice: Subject to any disclaimer, the term of this patent is extended or adjusted under 35 U.S.C. 154(b) by 0 days.

(21) Appl. No.: 11/814,104

(22) PCT Filed: Nov. 7, 2005

(86) PCT No.: PCT/EP2005/011968

§ 371 (c)(1),
(2), (4) Date: Jul. 17, 2007

(87) PCT Pub. No.: WO2006/074730

PCT Pub. Date: Jul. 20, 2006

(65) Prior Publication Data

US 2008/0071112 A1 Mar. 20, 2008

(30) Foreign Application Priority Data

Jan. 17, 2005 (EP) .................. 05447003

(51) Int. Cl.
*C07F 9/38* (2006.01)
(52) U.S. Cl. ..................................................... 562/16
(58) Field of Classification Search .................. 562/16
See application file for complete search history.

(56) References Cited

U.S. PATENT DOCUMENTS

| | | | | |
|---|---|---|---|---|
| 3,288,846 A | * | 11/1966 | Irani et al. ..................... | 562/16 |
| 3,458,281 A | * | 7/1969 | Demarcq ..................... | 423/307 |
| 3,459,793 A | | 8/1969 | Shen et al. | |
| 3,632,311 A | * | 1/1972 | Kovacs et al. ................ | 423/316 |
| 3,974,209 A | * | 8/1976 | Mitchell ........................ | 562/12 |
| 4,160,779 A | * | 7/1979 | Maier ........................... | 562/16 |
| 4,409,151 A | * | 10/1983 | Redmore et al. .............. | 562/14 |
| 4,657,705 A | * | 4/1987 | Miller et al. .................. | 562/17 |
| 5,105,047 A | * | 4/1992 | Waller ......................... | 585/515 |
| 5,459,249 A | * | 10/1995 | Bergfeld et al. ............. | 536/18.6 |
| 5,688,994 A | * | 11/1997 | Baysdon et al. ............... | 562/17 |
| 6,194,604 B1 | * | 2/2001 | Ma et al. ....................... | 562/17 |
| 6,238,637 B1 | * | 5/2001 | Heise et al. .................. | 423/316 |
| 6,440,380 B1 | * | 8/2002 | Heise et al. .................. | 423/299 |
| 6,476,256 B1 | * | 11/2002 | Heise et al. .................... | 562/17 |

FOREIGN PATENT DOCUMENTS

| | | |
|---|---|---|
| FR | 1342412 A | 11/1962 |
| JP | 57075990 A | 5/1982 |

OTHER PUBLICATIONS

Moedritzer et al., The Direct Synthesis of Alpha-Aminomethylphosphonic Acids, Mannich-Type Reactions with Orthophosphorous Acid, Journal of Organic Chemistry, American Chemical Society, Easton, US, vol. 31, May 1966, pp. 1603-1607.
Tramontiti et al., Further Advances in the Chemistry of Mannich Bases, Tetrahedron, Elsevier Science Publishers, Amsterdam, NL, vol. 46, No. 6, 1990, pp. 1791-1837.

* cited by examiner

*Primary Examiner*—Elvis O Price
(74) *Attorney, Agent, or Firm*—Husch Blackwell Sanders LLP

(57) ABSTRACT

A beneficial method for the manufacture of amino polyalkylene phosphonic acids, under substantial absence of hydrohalogenic acid, is disclosed. The method, in essence, is based on reacting narrowly defined ratios of phosphorous acid, an amine and a formaldehyde in presence of a heterogeneous Broensted acid catalyst. The inventive method is capable of yielding economically and quality operational/capacity advantages, in particular significantly reduced one-step cycle duration under exclusion of corrosion disadvantages and also is environmentally friendly without requiring, in that respect, anything more than nominal capital expenditures.

19 Claims, No Drawings

PROCESS FOR THE MANUFACTURE OF AMINOALKYLENEPHOSPHONIC ACID COMPOUNDS IN THE PRESENCE OF A HETEROGENEOUS CATALYST

CROSS REFERENCE TO RELATED APPLICATIONS

This application is a U.S. National Phase Application of International Application PCT Application No. PCT/EP2005/011968 filed on Nov. 7, 2005, which claims the benefit of priority from European Patent Application No. 05447003.4 filed on Jan. 17, 2005. The disclosures of International Application PCT Application No. PCT/EP2005/011968 and European Patent Application No. 05447003.4 are incorporated herein by reference.

This invention relates to a method for the manufacture of aminoalkylene phosphonic acid compounds, in particular compounds wherein all the available N—H functions, in a majority of the ammonia or amine raw material, have been alkylene phosphonated, under substantial exclusion of hydrohalogenic acid byproducts and intermediates. In more detail, aminoalkylene phosphonic acid compounds can be manufactured beneficially by reacting narrowly defined ratios of: phosphorous acid, an amine/ammonia, and a formaldehyde, in the presence of a heterogeneous, with respect to the reaction medium, acid catalyst.

Aminoalkylene phosphonic acid compounds are generally old in the art and have found widespread commercial acceptance for a variety of applications including water-treatment, scale-inhibition, detergent additives, sequestrants, marine-oil drilling adjuvants and as pharmaceutical components. It is well known that such industrial applications preferably require amino alkylene phosphonic acids wherein a majority of the N—H functions of the ammonia/amine raw material have been converted into the corresponding alkylene phosphonic acid. The art is thus, as one can expect, crowded and is possessed of methods for the manufacture of such compounds. The state-of-the-art manufacture of amino alkylene phosphonic acids is premised on converting phosphorous acid resulting from the hydrolysis of phosphorus trichloride or on converting phosphorous acid via the addition of hydrochloric acid which hydrochloric acid can be, in part or in total, added in the form of an amine hydrochloride.

The manufacture of amino alkylene phosphonic acids is described in GB 1.142.294. This art is premised on the exclusive use of phosphorus trihalides, usually phosphorus trichloride, as the source of the phosphorous reactant. The reaction actually requires the presence of substantial quantities of water, frequently up to 7 moles per mole of phosphorus trihalide. The water serves for the hydrolysis of the phosphorus trichloride to thus yield phosphorous and hydrochloric acids. Formaldehyde losses occur during the reaction which is carried out at mild temperatures in the range of from 30-60° C. followed by a short heating step at 100-120° C. The synthesis of aminomethyl phosphonic acids is described by Moedritzer and Irani, J. Org. Chem., May 1966, pages 1603-1607. Mannich-type reactions, and other academic reaction mechanisms, are actually disclosed. Optimum Mannich conditions require low-pH values such as resulting from the use of 2-3 moles of concentrated hydrochloric acid/mole of amine hydrochloride. This high acidity improves the yield and inhibits the oxidation of phosphite to phosphate. The formaldehyde component is added dropwise, at reflux temperature, to the reactant solution mixture of aminohydrochloride, phosphorous acid and concentrated hydrochloric acid. WO 96/40698 concerns the manufacture of N-phosphonomethyliminodiacetic acid by simultaneously infusing into a reaction mixture water, iminodiacetic acid, formaldehyde, a source of phosphorous acid and a strong acid. The source of phosphorous acid and strong acid are represented by phosphorus trichloride.

The use of phosphorus trichloride for preparing aminopolyalkylene phosphonic acids is, in addition, illustrated and emphasized by multiple authors such as Long et al. and Tang et al. in Huaxue Yu Nianhe, 1993 (1), 27-9 and 1993 34(3), 111-14 respectively. Comparable technology is also known from Hungarian patent application 36825 and Hungarian patent 199488. EP 125766 similarly describes the synthesis of such compounds in the presence of hydrochloric acid; along the same lines, JP 57075990 recommends preparing such compounds starting from phosphorous acid by reacting with an amine in the presence of concentrated hydrochloric acid.

U.S. Pat. No. 3,459,793 describes a process for the preparation of methylamino di(methylenephosphonic acid), in high yields, by converting two out of three N—H functions of ammonia to methylene phosphonic acid groups by reacting ammonia, formaldehyde and orthophosphorous acid. The third N—H function yields an N-methyl group. The reaction is optionally carried out in the presence of a water-soluble sulfate or sulfite catalyst such as alkali metal sulfate or alkali metal sulfite. The catalyst serves to inhibit the oxidation of phosphorous acid to phosphoric acid. The alkali metal ion promotes the formation of methylamino di(methylene phosphonic acid). The level of chloride ions is kept below 0.5% unless mixtures of methylamino di(methylene phosphonic acid) and amino tri(methylene phosphonic acid) are acceptable i.e. chloride ions promote the methylene phosphonic acid substitution of all available N—H functions.

It is a main object of this invention to provide a method for the manufacture of amino alkylene phosphonic acid (AAP) under substantial absence of hydrohalogenic, in particular hydrochloric, acid byproducts and intermediates. Another object of the invention concerns the manufacture of aminoalkylene phosphonic acids starting from ammonia or amine raw materials whereby all the available N—H functions are predominantly converted into the corresponding alkylene phosphonic acid derivatives. In particular, all the N—H functions in 50% or more of the amine raw material are reacted to yield alkylene phosphonic acid derivatives. Not more than 60%, preferably not more than 40%, of the reacted amine raw material, expressed in relation to the amine raw material wherein all the N—H functions have been converted into alkylene phosphonic acid (100%), carry at least one N—H function that has not been converted into an alkylene phosphonic acid derivative. It is another object of this invention to more efficiently use, during the manufacture of the AAP, the formaldehyde reactant which can suffer from the presence of hydrohalogenic acid in the formaldehyde distillate. Yet another object of this invention aims at producing AAP thereby substantially completely eliminating the release to the atmosphere, or the abatement by e.g. thermal oxidation, of environmentally less desirable byproducts such as methylchloride. Another object of this invention aims at generating AAP manufacturing technology, which is not affected by substantial corrosion problems. Yet another object of this invention aims at providing efficient, non-capital intensive, AAP manufacturing technology. Still another object of this invention aims at generating acid catalysts for the manufacture of AAP under substantial absence of hydrohalogenic acids or precursors therefore. Yet another desirable object of the invention seeks to provide an effective acid catalyst which can be recycled with or without regeneration and which allows the obtainment of reaction products without undue separation and/or purification measures. The foregoing and other objects can now be met by means of the inventive technology herein as follows.

The "percentage" or "%" indications hereinafter stand, unless defined differently, for "percent by weight". The terms "phosphonic acid" and "phosphonate" can be used, throughout the description and claims, interchangeably. The reactant designations "phosphorous acid" and "amine" define the individual reactants per sé and the precursors therefore. The term "formaldehyde" designates interchangeably formaldehyde, sensu stricto, aldehydes and ketones. The term "amine raw material" can designate interchangeably "ammonia" and/or "amine".

It has now been discovered that aminoalkylene phosphonic acids can be manufactured, in presence of not more than 0.4% by weight, expressed in relation to the level of the phosphorous acid component (100%), of hydrohalogenic acid, whereby all the available N—H functions in 50% or more of the amine raw material are converted to the corresponding alkylene phosphononic acid by reacting:

(a): phosphorous acid (b): an amine; and (c): a formaldehyde;

in reactant ratios as follows:

(c):(a) of from 5:1 to 0.25:1;

(a):(b) of from 0.05:1 to 2:1;

(c):(b) of from 0.05:1 to 5:1; and wherein (a) and (c) stand for the number of moles to be used and (b) represents the number of moles multiplied by the number of N—H functions in the amine, in the presence of an acid catalyst, said acid catalyst (d) being a heterogeneous, with respect to the reaction medium, Broensted acid catalyst selected from the group of:

(1) solid acidic metal oxide combinations as such or supported onto a carrier material;

(2) cation exchange resins selected from the group comprising copolymers of styrene, ethylvinyl benzene and divinyl benzene, functionalized so as to graft $SO_3H$ moieties onto the aromatic group and perfluorinated resins (3) organic sulfonic and carboxylic Broensted acids which are substantially immiscible in the reaction medium at the reaction temperature;

(4) an acid catalyst derived from:
   (i) the interaction of a solid support having a lone pair of electrons onto which is deposited an organic Broensted acid; or
   (ii) the interaction of a solid support having a lone pair of electrons onto which is deposited a compound having a Lewis acid site;
   (iii) heterogeneous solids functionalized by chemical grafting with a Broensted acid group or a precursor therefore, and (5) heterogeneous heteropolyacids of the general formula $H_xPM_yO_z$ wherein P is selected from phosphorus and silicon and M is selected from W and Mo and combinations thereof followed by recovering the amino alkylene phosphonic acid formed in a manner known per sé.

The phosphorous acid component can be used as such or can be entered in its P-oxide form. Phosphorous acid and the corresponding P-oxides can be derived from any suitable precursor including naturally occurring phosphorus containing rocks which can be converted, in a known manner, to elemental phosphorus followed by oxidation to P-oxides and possibly phosphorous acid. The phosphorous acid reactant can also be prepared, starting from hydrolyzing $PCl_3$ and purifying the phosphorous acid so obtained by eliminating hydrochloric acid and other chloride intermediates originating from the hydrolysis.

In a preferred embodiment, the phosphorous acid purification is applied to reduce the level of chloride to below 0.4%, preferably below 2000 parts-per-million (ppm) or smaller, more preferably 200 ppm or smaller, expressed in relation to the phosphorous acid (100%).

In general, the method herein is conducted in the presence of not more than 0.4% of hydrochloric acid, preferably 2000 ppm or less, more preferably 200 ppm or less, expressed in relation to the phosphorous acid component.

While the preparation of phosphorous acid by the direct oxidation of elemental phosphorus and hydrolysis of the resulting P-oxides is known to be difficult, various technologies can be economically acceptable in that respect. Canadian patent application 2.070.949 divulges a method for the manufacture of phosphorous acid, or the corresponding $P_2O_3$ oxide, by introducing gaseous phosphorus and steam water into a gas plasma reaction zone at a temperature in the range of 1500° K to 2500° K to thus effect conversion to $P_2O_3$ followed by rapidly quenching the phosphorus oxides at a temperature above 1500° K with water to a temperature below 1100° K to thus yield $H_3PO_3$ of good purity. In another approach, phosphorus(I) and (III) oxides can be prepared by catalytic reduction of phosphorus(V) oxides as described in U.S. Pat. No. 6,440,380. The oxides can be reacted with water to thus yield phosphorous acid. EP-A-1.008.552 discloses a process for the preparation of phosphorous acid by oxidizing elemental phosphorus in the presence of an alcohol to yield P(III) and P(V) esters followed by selective hydrolysis of the phosphite ester into phosphorous acid. WO 99/43612 describes a catalytic process for the preparation of P(III) oxyacids in high selectivity. The catalytic oxidation of elemental phosphorus to phosphorous oxidation levels is also known from U.S. Pat. Nos. 6,476,256 and 6,238,637.

In another approach, phosphorous acid can be manufactured beneficially by reacting phosphorus trichloride with a reagent which is either a carboxylic acid or a sulfonic acid or an alcohol. The $PCl_3$ reacts with the reagent under formation of phosphorous acid and an acid chloride in the case an acid reagent or a chloride, for example an alkylchloride, originating from the reaction of the $PCl_3$ with the corresponding alcohol. The chlorine containing products, e.g. the alkylchloride and/or the acid chloride, can be conveniently separated from the phosphorous acid by methods known in the art e.g. by distillation or phase separation. While the phosphorous acid so manufactured can be used as such in the claimed arrangement, it can be desirable and it is frequently preferred to purify the phosphorous acid formed by substantially eliminating or diminishing the levels of chlorine containing products and non-reacted raw materials. Such purifications are well known and fairly standard in the domain of the relevant manufacturing technology. Suitable examples of such technologies include the selective adsorption of the organic impurities on active carbon or the use of aqueous phase separation for the separation of the phosphorous acid component. Information pertinent to the reaction of phosphorous trichloride with a reagent such as a carboxylic acid or an alcohol can be found in Kirk-Othmer, Encyclopedia of Chemical Technology, in chapter Phosphorus Compounds, Dec. 4, 2000, John Wiley & Sons Inc.

In one preferred execution herein, the phosphorous acid reactant used in the method of the invention is represented by species prepared under substantial exclusion of halogens. Such methods for preparing phosphorous acid under the exclusion of halogens are well known in the domain of the technology. Specific examples of methods which can be used for preparing such phosphorous acid reactants are summarized hereinafter.

In one method (i), phosphorous acid can be prepared by contacting elemental phosphorus, preferably tetraphosphorus, with water, at a temperature below 200° C., in the presence of a catalyst effective to promote oxidation of phosphorus by reaction with water such as a noble metal catalyst e.g. Pd, to thus yield phosphorous acid in high selectivity. This process is described in U.S. Pat. No. 6,238,637 B1. Substantially identical disclosures can be taken from WO 99/43612 and U.S. Pat. No. 6,476,256 B1. In another approach (ii), predominantly P(III) species, such as phosphorous acid, can be prepared by contacting P(V) species with a reducing agent such as hydrogen in the presence of a reducing catalyst. This process is described in detail in U.S. Pat. No. 6,440,380 B1. In yet another process (iii), phosphorous acid can be manufactured by the selective hydrolysis of phosphite esters. A hydrolysis feed mixture comprising phosphite esters and phosphate esters is contacted with liquid water and steam to selectively hydrolyse the phosphite esters to phosphorous acid. EP 1.008.552 A1 provides an enabling description of this technology.

The essential amine component can be represented broadly by conventional nitrogen-containing reactants. More specifically, the amine component can be selected from the group of:

ammonia;

primary and secondary amines containing individual hydrocarbon groups having from 1 to 100, preferably 1 to 50, carbon atoms, said hydrocarbon moieties can be represented by straight or branched linear alkyl moieties or cyclic alkyl moieties or aromatic or polyaromatic moieties or combinations thereof;

polyamines; and primary and secondary amines and polyamines containing alkoxylated or thioalkoxylated radicals and/or functional groups including functionalized silyl groups such as trialkyl silyl, hydroxyl, carboxylic acid or sulfonic acid or esters of such acids or combinations thereof.

Specific examples of alkylamines are methylamine, ethylamine, butyl amine, octyl amine, decyl amine, dodecyl amine, stearyl amine, dimethyl amine, diethyl amine, dibutyl amine, naphthyl amine, benzyl amine, aniline and cyclohexyl amine. Also primary or secondary aliphatic amines containing substituted alkyl groups can be used.

Suitable polyamine species include ethylene diamine, diethylene triamine, triethylene tetramine, di(propylene)ethylene tetramine, di(hexamethylene) triamine, hexamethylene diamine and polymeric amines such as polyethylene imine and polyallylamine.

While the amine may be used in the free form, it is often preferred to use it in the form of a salt, such as a sulfate.

The essential formaldehyde component is a well known commodity ingredient. Formaldehyde generally is produced and sold as water solutions containing variable, frequently minor, e.g. 0.3-3%, amounts of methanol and are reported on a 37% formaldehyde basis. Formaldehyde solutions exist as a mixture of oligomers. Formaldehyde precursors can, for example, be represented by paraformaldehyde, a solid mixture of linear poly(oxymethylene glycols) of usually fairly short, n=8-100, chain length, and cyclic trimers and tetramers of formaldehyde designated by the terms trioxane and tetraoxane respectively. The formaldehyde component can also be represented by aldehydes and ketones having the formula $R_1R_2C{=}O$ wherein $R_1$ and $R_2$ can be identical or different and are selected from the group of hydrogen and organic radicals. When $R_1$ is hydrogen, the material is an aldehyde. When both $R_1$ and $R_2$ are organic radicals, the material is a ketone. Species of useful aldehydes are, in addition to formaldehyde, acetaldehyde, caproaldehyde, nicotinealdehyde, crotonaldehyde, glutaraldehyde, p-tolualdehyde, benzaldehyde, naphthaldehyde and 3-aminobenzaldehyde. Suitable ketone species for use herein are acetone, methylethylketone, 2-pentanone, butyrone, acetophenone and 2-acetonyl cyclohexanone.

The technology herein requires the presence, as an essential component, of a heterogeneous Broensted acid catalyst. The Broensted properties represent the capabilities of supplying protons. The term heterogeneous means that the acid catalyst is substantially insoluble in the reaction medium, at the reaction conditions, or substantially immiscible, thus liquid, in the reaction medium at the reaction conditions. The insoluble and/or immiscible nature of the catalyst can be ascertained routinely e.g. based on visible observation. Broensted acidity can also originate from Lewis acid properties after coordination of the Lewis site on the catalyst with a lone pair of electrons in a coordination partner e.g. water. The Broensted acidity can also be derived from the addition of a Lewis acid e.g. $BF_3$ to the Broensted acid catalyst precursor having a lone pair of electrons and being capable of coordinating with the Lewis acid e.g. silica.

The Broensted properties of any given acid catalyst are readily and routinely ascertainable. As an example, the Broensted acidity can be determined, for thermally stable inorganic products, by e.g. thermal desorption of isopropylamine followed by using a micro-balance in accordance with the method of R. J. Gorte et al., J. Catal. 129, 88, (1991) and 138, 714, (1992).

The heterogeneous catalyst, having Broensted acid properties, can, by way of example, be represented by species of discretionary selected subclasses, namely:

(1) solid catalysts represented by acidic metal oxide combinations which can be supported onto usual carrier materials such as silica, carbon, silica-alumina combinations or alumina. These metal oxide combinations can be used as such or with inorganic or organic acid doping. Suitable examples of this class of catalysts are amorphous silica-alumina, acid clays, such as smectites, inorganic or organic acid treated clays, pillared clays, zeolites, usually in their protonic form, and metal oxides such as $ZrO_2$—$TiO_2$ in about 1:1 molar combination and sulfated metal oxides e.g. sulfated $ZrO_2$. Other suitable examples of metal oxide combinations, expressed in molar ratios, are: $TiO_2$—$SiO_2$ 1:1 ratio; and $ZrO_2$—$SiO_2$ 1:1 ratio.

(2) several types of cation exchange resins can be used as acid catalyst to carry out the reaction of an amine, phosphorous acid and a formaldehyde. Most commonly, such resins comprise copolymers of styrene, ethylvinyl benzene and divinyl benzene functionalized so as to graft $SO_3H$ groups onto the aromatic groups. Such resins are used as acidic catalysts in numerous commercial productions like e.g. in methyl t-butyl ether manufacturing from methanol and isobutene or in bisphenol A manufacturing starting from acetone and phenol.

These acidic resins can be used in different physical configurations such as in gel form, in a macro-reticulated configuration or supported onto a carrier material such as silica or carbon or carbon nanotubes. Other types of resins include perfluorinated resins carrying carboxylic or sulfonic acid groups or both carboxylic and sulfonic acid groups. Known examples of such resins are: NAFION™, FLEMION™ and NEOSEPTA-F™. The fluorinated resins can be used as such or supported onto an inert material like silica or carbon or carbon nanotubes entrapped in a highly dispersed network of metal oxides and/or silica.

FLEMION is a Trademark of Asahi Glass, Japan
NEOSEPTA is a Trademark of Tokuyama Soda, Japan
NAFION is a trademark of DuPont, USA.

(3) a Broensted acid catalyst, such as an organic Broensted acid, which is substantially insoluble or immiscible in the reaction medium. The catalyst can form, at the reaction conditions, in particular the reaction temperature, a second liquid phase and can be recovered at the end of the reaction by conventional techniques such as filtration or phase separation. Examples of suitable acidic reagents include highly fluorinated, which means that 50% or more of the hydrogen atoms attached to the carbon atoms have been substituted by fluorine atoms, long chain sulfonic or carboxylic acids like perfluorinated undecanoic acid or more in particular perfluorinated carboxylic acid and perfluorinated sulfonic acids having from 6 to 24 carbon atoms. Such perfluorinated acid catalysts can be substantially immiscible in the reaction medium. The reaction will take place in a reactor under continuous stirring to ensure an adequate dispersion of the acid phase into the aqueous phase. The acidic reagent may itself be diluted into a water insoluble phase such as e.g. a water insoluble ionic liquid;

(4) heterogeneous solids, having usually a lone pair of electrons, like silica, silica-alumina combinations, alumina, zeolites, silica, activated charcoal, sand and/or silica gel can be used as support for a Broensted acid catalyst, like methane sulfonic acid or para-toluene sulfonic acid, or for a compound having a Lewis acid site, such as $SbF_5$, to thus interact and yield strong Broensted acidity. Heterogeneous solids, like zeolites, silica, or mesoporous silica e.g. MCM-41 or -48, or polymers like e.g. polysiloxanes can be functionalized by chemical grafting with a Broensted acid group or a precursor therefore to thus yield acidic groups like sulfonic and/or carboxylic acids or precursors therefore. The functionalization can be introduced in various ways known in the art like: direct grafting on the solid by e.g. reaction of the SiOH groups of the silica with chlorosulfonic acid; or can be attached to the solid by means of organic spacers which can be e.g. a perfluoro alkyl silane derivative. Broensted acid functionalized silica can also be prepared via a sol gel process, leading to e.g. a thiol functionalized silica, by co-condensation of $Si(OR)_4$ and e.g. 3-mercaptopropyl-tri-methoxy silane using either neutral or ionic templating methods with subsequent oxidation of the thiol to the corresponding sulfonic acid by e.g. $H_2O_2$. The functionalized solids can be used as is, i.e. in powder form, in the form of a zeolitic membrane, or in many other ways like in admixture with other polymers in membranes or in the form of solid extrudates or in a coating of e.g. a structural inorganic support e.g. monoliths of cordierite; and (5) heterogeneous heteropolyacids having most commonly the formula $H_xPM_yO_z$. In this formula, P stands for a central atom, typically silicon or phosphorus. Peripheral atoms surround the central atom generally in a symmetrical manner. The most common peripheral elements, M, are usually Mo or W although V, Nb, and Ta are also suitable for that purpose. The indices xyz quantify, in a known manner, the atomic proportions in the molecule and can be determined routinely. These polyacids are found, as is well known, in many crystal forms but the most common crystal form for the heterogeneous species is called the Keggin structure. Such heteropolyacids exhibit high thermal stability and are non-corrosive. The heterogeneous heteropolyacids are preferably used on supports selected from silica gel, kieselguhr, carbon, carbon nanotubes and ion-exchange resins. A preferred heterogeneous heteropolyacid herein can be represented by the formula $H_3PM_{12}O_{40}$ wherein M stands for W and/or Mo. Examples of preferred PM moieties can be represented by $PW_{12}$, $PMo_{12}$, $PW_{12}/SiO_2$, $PW_{12}/carbon$ and $SiW_{12}$.

The heterogeneous catalyst herein is generally used in levels well known in the domain of the technology. The ultimate criteria for the determination of the catalyst level resides, of course, in the completeness of the reaction i.e. the conversion of phosphorous acid to phosphonic acid compounds. The quantitative catalyst level can thus, in that respect, be optimized routinely. Considering that the catalyst can be used throughout the entire reaction medium, e.g. a dispersed immiscible catalyst, or locally e.g. in a fixed bed or in a membrane or equivalent configurations, it is evident that in such cases the quantity of the catalyst cannot be defined in relation to the co-reactants. Irrespective of a correlation between the relative levels of the reactants, such as the amine and the catalyst, it was experimentally established that very low levels of the catalyst can yield, within the context of the inventive technology, beneficially high conversion to phosphonic acid. In particular, it was found that, in a batch process arrangement e.g. in a continuously stirred tank reactor (CSTR), the ratio of the amine (b) in direct (CSTR) contact with the heterogeneous catalyst (d) is generally in the range of from 40:1 to 1:5, (b) being expressed as the number of moles multiplied by the number of N—H functions in the amine. The catalyst (d) is expressed as the number of catalyst proton equivalents. In a fixed bed configuration only the amine (b) directly in contact with the heterogeneous catalyst (d) will be considered. In the fixed bed configuration the ratio of the amine (b) to the catalyst (d), expressed as indicated for the CSTR, is frequently in the range of from 10:1 to 1:40.

The heterogeneous Broensted acid catalyst can be used in many operational manufacturing arrangements well known in the domain of the technology. The catalyst can, for example, be used in a fixed bed configuration or in a continuously stirred tank reactor (CSTR) or in a membrane arrangement or suspended in the reaction mixture or in admixture with the reaction mixture. It is particularly noteworthy that the heterogeneous catalyst offers significant operational and economic advantages. The catalyst can, for example, be recycled and reused generally as such although a minimal non-destructive treatment, e.g. water or acid rinsing, can be in order.

The reaction in accordance with this invention is conducted in a manner routinely known in the domain of the technology. As illustrated in the experimental showings, the method can be conducted by combining the essential reactants and heating the reaction mixture to a temperature usually within the range of from 45° C. to 200° C., and higher temperatures if elevated pressures are used, more preferably 70° C. to 150° C. The upper temperature limit actually aims at preventing any substantially undue thermal decomposition of the phosphorous acid reactant. It is understood and well known that the decomposition temperature of the phosphorous acid reactant, and more in general of any other individual reactant, can vary depending upon additional physical parameters, such as pressure and the qualitative and quantitative parameters of the co-reactants in the reaction mixture.

The inventive reaction can be conducted at ambient pressure and, depending upon the reaction temperature, under distillation of water, thereby also eliminating a minimal amount of non-reacted formaldehyde. The duration of the reaction can vary from a relatively short time, e.g. 30 minutes, to an extended period of e.g. 4 hours. This duration generally includes the gradual addition, during the reaction, of formaldehyde and possibly other reactants. In one method set up, the phosphorous acid, the amine and the acid catalyst are added to the reactor followed by heating this mixture under gradual addition of the formaldehyde component starting at a temperature e.g. in the range of from 70° C. to 150° C. This reaction can be carried out under ambient pressure with or without distillation of usually water and some non-reacted formaldehyde.

In another operational arrangement, the reaction can be conducted in a closed vessel under autogeneous pressure built up. In this method, the reactants, in total or in part, are added to the reaction vessel at the start. In the event of a partial reactant mixture, the additional reactant can be gradually added, alone or with any one or more of the other reactants, as soon as the effective reaction temperature has been reached. The gradual addition of formaldehyde during the effective reaction is illustrated in the Examples. The formaldehyde reactant can, for example, be added gradually during the reaction alone or with parts of the amine or the phosphorous acid.

In yet another operational sequence, the reaction can be conducted in a combined distillation and pressure arrangement. Specifically, the reaction vessel containing the reactant mixture is kept under ambient pressure at the selected reaction temperature. The mixture is then, possibly continuously, circulated through a reactor operated under autogeneous (autoclave principle) pressure built up thereby gradually adding the formaldehyde or additional reactants in accordance with needs. In a preferred execution, the closed reactor can contain the heterogeneous Broensted acid catalyst in whatever configuration is suitable for the contemplated reaction. The reaction is substantially completed under pressure and the reaction mixture then leaves the closed vessel and is recirculated into the reactor where distillation of water and other non-reacted ingredients can occur depending upon the reaction variables, particularly the temperature.

The foregoing process variables thus show that the reaction can be conducted by a variety of substantially complementary arrangements. The reaction can thus be conducted as a batch process by heating the initial reactants, usually the phosphorous acid, the amine and the acid catalyst in a (1) closed vessel under autogeneous pressure built up, or (2) under reflux conditions, or (3) under distillation of water and minimal amounts of non-reacted formaldehyde, to a temperature preferably in the range of from 70° C. to 150° C. whereby the formaldehyde component is added, as illustrated in the Examples, gradually during the reaction. In a particularly preferred embodiment, the reaction is conducted in a closed vessel at a temperature in the range of from 100° C. to 150° C., coinciding particularly with the gradual addition of formaldehyde.

In another approach, the reaction is conducted as a continuous process, possibly under autogeneous pressure, whereby the reactants are continuously injected into the reaction mixture, at a temperature preferably in the range of from 70° C. to 150° C. and the phosphonic acid reaction product is withdrawn on a continuous basis.

In yet another arrangement, the method can be represented by a semi-continuous set-up whereby the phosphonic acid reaction is conducted continuously whereas preliminary reactions between part of the components can be conducted batch-wise.

The examples hereinafter illustrate the claimed technology and facilitate its understanding.

EXAMPLE 1

Aminopolymethylene phosphonic acid compounds were prepared by reacting the listed ingredients in the stated proportions.

| Reactant | g | mole(s) |
|---|---|---|
| Phosphorous acid | 301.35 | 3.675 |
| Amberlyst 36 dry | 150.0 | |
| Ammonia (25%-solution) | 81.6 | 1.2 |
| Formaldehyde (36.6%-solution) | 309.9 | 3.78 |

A mixture of the phosphorous acid, the Amberlyst 36 and the ammonia is heated up, under stirring, to 105° C. starting from which temperature the formaldehyde was gradually added, under distillation, over a period of 4 hours and 20 minutes.

The reaction product was analyzed with a 31P-NMR spectroscopic method. It was found that major levels of aminotrimethylene phosphonic acid (ATMP) and N-methylene-imino bis(methylene phosphonic acid) (N-MeIBMPA) were present in the reaction product, as follows:

| | |
|---|---|
| ATMP | 67.5%; |
| N-MeIBMPA | 6.3%; and |
| $H_3PO_3$ | 15.9%. |

EXAMPLE 2

Further amino polymethylene phosphonic acids were prepared by reacting in the operational sequence of Example 1, except for the duration of the formaldehyde addition, the listed materials as follows:

| Reactant | g | mole(s) |
|---|---|---|
| Phosphorous acid | 100.45 | 1.225 |
| Amberlyst 15 wet resin | 125.0 | |
| Ammonia (25%-solution) | 27.2 | 0.4 |
| Formaldehyde (36.6%-solution) | 103.27 | 1.26 |

The formaldehyde was added, starting from 105° C., under distillation, over a period of 2 hours and 30 minutes.

The reaction product analyzed thereby using the method of Example 1 showed the following major component levels.

| | |
|---|---|
| ATMP | 62.7%; |
| N-MeIBMPA | 8.4%; and |
| $H_3PO_3$ | 21.1%. |

EXAMPLE 3

An ATMP composition was made by reacting the listed ingredients in the stated proportions.

| Reactant | g | mole(s) |
|---|---|---|
| Phosphorous acid | 47.71 | 0.5697 |
| Ammonia (32% solution) | 10.08 | 0.1899 |
| Formaldehyde (36.6% solution) | 49.03 | 0.5981 |
| Perfluoro-undecanoic acid | 12.50 | 0.02215 |

The perfluoro-undecanoic acid catalyst is immiscible in the reaction medium at the reaction conditions. All the reactants, except the formaldehyde, were charged into a pressure autoclave before starting the heating. The formaldehyde was added starting at a temperature of 120° C. during a period of 2 hours.

The reaction product, analyzed in accordance with the method of Example 1, contained the following major compounds.

| | |
|---|---|
| ATMP | 58.6% |
| N-MeIBMPA | 14.6% |
| $H_3PO_3$ | 14.4% |
| $H_3PO_4$ | 5.6% |

Further aminopolymethylene phosphonic acid compositions were made by reacting the listed ingredients as set forth below.

| Reactant | Example N° | g | mole(s) |
|---|---|---|---|
| Phosphorous acid | 4 | 46.71 | 0.5697 |
| Idem | 5, 6 | 93.43 | 1.1394 |
| Perfluoroundecanoic acid | 6 | 3.21 | 0.005697 |
| Idem | 5 | 6.42 | 0.01139 |
| Idem | 4 | 7.45 | 0.0132 |
| Ammonia (32% solution) | 4 | 10.08 | 0.1899 |
| Idem | 5, 6 | 20.17 | 0.3798 |
| Formaldehyde (36.6% sol.) | 4 | 49.03 | 0.5981 |
| Idem | 5, 6 | 98.04 | 1.1962 |

The reaction mixture was prepared by adding the phosphorous acid, the perfluoro undecanoic acid and the ammonia to the reactor under ambient conditions. The reaction mixture was then heated to 120° C. and the formaldehyde was gradually added, starting from 120° C., over a period of 120 minutes.

The reaction products analyzed in accordance with the method of Example 1 confirmed the formation of major levels of phosphonic acid components as follows.

| Example N° | ATMP-% | N-MeIBMPA-% | $H_3PO_3$-% | $H_3PO_4$-% |
|---|---|---|---|---|
| 4 | 61.4 | 15.3 | 9.2 | 6.6 |
| 5 | 59.2 | 15.0 | 8.3 | 6.8 |
| 6 | 59.0 | 15.1 | 8.4 | 6.7 |

The analytical results confirm the formation of high levels of desirable phosphonic acid compounds with the further observation that the reaction conditions offer ample leeway for optimization as is shown by the fairly substantial levels of non-reacted phosphorous acid and the concurrent decrease in the formation of phosphoric acid.

Additional aminopolymethylene phosphonic acid compositions were prepared as follows.

EXAMPLE 7

114 g Commercial wet Amberlyst 36 resin containing on average 56% of water was soaked several times with 100 g of a solution of 87.14% phosphorous acid in water, each time the soaked resin is agitated for 15 minutes followed by separating the aqueous phase and replacing it with a fresh solution of phosphorous acid. This soaking step was repeated three times and the Amberlyst resin so obtained was found to contain a mixture of 52.37 g of phosphorous acid and 11.46 g of water. Inasmuch as in this method, we need 67.80 g of phosphorous acid, 15.43 g of $H_3PO_3$ were added to thus complement the quantity present in the catalyst. The phosphorous acid ingredient was added to the Amberlyst catalyst followed by stirring the mixture at room temperature under addition of 14.34 g of ammonia (32% solution). To this mixture was subsequently added, under agitation in a pressure autoclave starting at 125° C. during a period of 60 minutes, 69.70 g, (0.8505 mole), of formaldehyde (36.6% solution). The resin is thereafter separated, from the reaction mixture, by filtration and can be used as such as a catalyst in the following Example.

EXAMPLE 8

The recycled catalyst of Example 8 was mixed, at room temperature, with 67.8 g, (0.8268 mole), of phosphorous acid and 14.34 g, (0.8505 mole), of ammonia (32% solution). 69.70 g, (0.8505 mole), of formaldehyde (36.6% solution) were added to that mixture, in a pressure autoclave over a period of 60 minutes starting at 125° C.

The reaction products of Examples 7 and 8, analyzed in accordance with the method of Example 1, showed that major levels of phosphonic acids were formed as follows.

| Example N° | ATMP-% | N-MeIBMPA-% | $H_3PO_3$-% | $H_3PO_4$-% |
|---|---|---|---|---|
| 7 | 57 | 9.5 | 12 | 3 |
| 8 | 57.4 | 9.7 | 12.3 | 3.4 |

The data illustrate the beneficial recycling of the catalyst in the synthesis of aminomethylene phosphonic acids.

The invention claimed is:

1. A method for the manufacture of amino alkylene phosphonic acid, comprising reacting in presence of not more than 0.4% by weight, expressed in relation to the level of the phosphorous acid component (100%), of hydrohalogenic acid:
   (a): phosphorous acid;
   (b): an amine; and
   (c): a formaldehyde;
   in reactant ratios as follows:
   (a):(b) of from 0.05:1 to 2:1;
   (c):(b) of from 0.05:1 to 5:1; and
   (c):(a) of from 5:1 to 0.25:1;
   wherein (a) and (c) stand for the number of moles to be used and (b) represents the number of moles multiplied by the number of N—H functions in the amine, in the presence of a heterogeneous, with respect to the reaction medium, Broensted acid catalyst selected from the group of:

(1) solid acidic metal oxide combinations or supported onto a carrier material;

(2) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;

(3) organic sulfonic and carboxylic Broensted acids which are substantially immiscible in the reaction medium at the reaction temperature;

(4) an acid catalyst derived from:
  (i) the interaction of a solid support having a lone pair of electrons onto which is deposited an organic Broensted acid; or
  (ii) the interaction of a solid support having a lone pair of electrons onto which is deposited a compound having a Lewis acid site;
  (iii) heterogeneous solids functionalized by chemical grafting with a Broensted acid group or a precursor therefore, and (5) heterogeneous heteropolyacids of the general formula $H_xPM_yO_z$ wherein P is selected from phosphorus and silicon and M is selected from W and Mo and combinations thereof followed by recovering the amino alkylene phosphonic, whereby all the available N—H functions in 50% or more of the amine raw material are converted to the corresponding alkylene phosphonic acids.

2. The method in accordance with claim 1 wherein the reactant ratios are as follows:
(a):(b) of from 0.1:1 to 1.50:1;
(c):(b) of from 0.2:1 to 2:1; and
(c):(a) of from 3:1 to 0.5:1.

3. The method in accordance with claim 1 wherein the reaction is carried out at a temperature in the range of from 45° C. to 200° C.

4. The method in accordance with claim 1 wherein the reactant ratios are as follows:
(a):(b) of from 0.4:1 to 1.0:1.0;
(c):(b) of from 0.4:1 to 1.5:1; and
(c):(a) of from 2:1 to 1.0:1.

5. The method in accordance with claim 3 wherein the reaction is carried out at a temperature in the range of from 70° C. to 150° C. combined with an approach selected from:
conducting the reaction under ambient pressure with or without distillation of water and non-reacted formaldehyde;
in a closed vessel under autogeneous pressure built up;
in a combined distillation and pressure arrangement whereby the reaction vessel containing the reactant mixture is kept under ambient pressure at the reaction temperature followed by circulating the reaction mixture through a reactor operated under autogeneous pressure built up thereby gradually adding the formaldehyde; and
a continuous process arrangement, possibly under autogeneous pressure built up, whereby the reactants are continuously injected into the reaction mixture and the phosphonic acid reaction product is withdrawn on a continuous basis.

6. The method in accordance with claim 1 wherein the amine is selected from the group of:
ammonia;
primary and secondary amines containing individual hydrocarbon groups having from 1 to 100 carbon atoms, said hydrocarbon moieties being represented by straight or branched linear alkyl moieties or cyclic alkyl moieties or aromatic or polyaromatic moieties or combinations thereof;
polyamines; and
primary and secondary amines or polyamines containing alkoxylated or thioalkoxylated radicals and/or functional groups including trialkyl silyl, hydroxyl, carboxylic acid or sulfonic acid or esters of such acids or combinations thereof.

7. The method in accordance with claim 6 wherein the amine is selected from the group of methyl amine, ethyl amine, butyl amine, octyl amine, decyl amine, dodecyl amine, stearyl amine, dimethyl amine, diethyl amine, dibutyl amine, naphthyl amine, benzyl amine, aniline and cyclohexyl amine.

8. The method in accordance with claim 6 wherein the amine is a polyamine selected from the group of ethylene diamine, diethylene triamine, triethylene tetramine, di(propylene)ethylene tetramine, di(hexylene) triamine, polyethylene imine and polyallylamines.

9. The method in accordance with claim 1 wherein the phosphorous acid reactant is prepared, in presence of not more than 2000 parts-per-million (ppm) of hydrohalogenic acid.

10. The method in accordance with claim 1 wherein the phosphorous acid is prepared, in the presence of not more than 0.2% by weight of hydrohalogenic acid, expressed in relation to the level of phosphorous acid (100%):
(i) by contacting elemental phosphorus with water at a temperature below 200° C. in the presence of a catalyst effective to promote oxidation of phosphorus by reaction with water; or
(ii) by contacting P(V) species with a reducing agent such as hydrogen in the presence of a reducing catalyst; or
(iii) by contacting a hydrolysis feed mixture comprising phosphite esters and phosphate esters with liquid water and steam to thereby hydrolyze the phosphite esters to phosphorous acid.

11. The method in accordance with claim 10 wherein the elemental phosphorus is tetraphosphorus.

12. The method in accordance with claim 1 wherein the phosphorous acid is prepared by reacting phosphorus trichloride with a reagent from the group of: a carboxylic acid; a sulfonic acid; and an alcohol followed by eliminating the chlorine containing products formed and the non-reacted raw materials by distillation or phase separation.

13. The method in accordance with claim 12 by substantially eliminating chlorine containing products to a level of 2000 parts-per-million (ppm) or smaller, expressed in relation to the level of the phosphorous acid component (100%).

14. The method in accordance with claim 1 wherein the phosphorous acid is prepared by hydrolyzing phosphorus trichloride followed by the elimination of hydrochloric acid and other chloride intermediates to a level of not more than 2000 ppm, expressed in relation to the level of phosphorous acid (100%).

15. The method in accordance with claim 1 wherein the organic Broensted acid is selected from fluorinated carboxylic acids and fluorinated sulfonic acids having from 6 to 24 carbon atoms in the hydrocarbon chain.

16. The method in accordance with claim 15 wherein the Broensted acid catalyst is represented by perfluorinated undecanoic acid.

17. The method in accordance with claim 1 wherein the PM moiety in the heterogeneous heteropolyacid is selected from the group of $PW_{12}$, $PMo_{12}$, $PW_{12}/SiO_2$, $PW_{12}$/carbon and $SiW_{12}$.

18. The method in accordance with claim 1 wherein the reaction is carried out in an arrangement selected from a continuously stirred tank reactor (CSTR) and a fixed bed whereby the ratio of the amine (b), in direct contact with the heterogeneous catalyst, to the heterogeneous catalyst (d) is, in the CSTR, in the range of from 40:1 to 1:5, and in the fixed bed in the range of from 10:1 to 1:40, (d) being expressed as the number of catalyst proton equivalents.

19. The method in accordance with claim 6 wherein the individual hydrocarbon groups in the primary and secondary amines have from 1 to 50 carbon atoms.

* * * * *